(12) United States Patent
Kukkar et al.

(10) Patent No.: US 10,765,529 B2
(45) Date of Patent: Sep. 8, 2020

(54) ARTICULATING INTERVERTEBRAL DEVICES, RELATED TOOLS, SYSTEMS, AND METHODS

(71) Applicant: CTL Medical Corporation, Addison, TX (US)

(72) Inventors: Nitin Kukkar, Quincy, IL (US); Jon Wing, Crystal Lake, IL (US); Jon Suh, Ambler, PA (US); Sean Suh, Milltown, NJ (US)

(73) Assignee: CTL Medical Corporation, Addison, TX (US)

( * ) Notice: Subject to any disclaimer, the term of this patent is extended or adjusted under 35 U.S.C. 154(b) by 462 days.

(21) Appl. No.: 14/974,174

(22) Filed: Dec. 18, 2015

(65) Prior Publication Data

US 2017/0172759 A1    Jun. 22, 2017

(51) Int. Cl.
| | | |
|---|---|---|
| *A61F 2/00* | (2006.01) | |
| *A61F 2/44* | (2006.01) | |
| *A61B 17/56* | (2006.01) | |
| *A61F 2/46* | (2006.01) | |
| *A61F 2/28* | (2006.01) | |
| *A61F 2/30* | (2006.01) | |

(52) U.S. Cl.
CPC .......... *A61F 2/4465* (2013.01); *A61F 2/4611* (2013.01); *A61F 2002/2835* (2013.01); *A61F 2002/3093* (2013.01); *A61F 2002/30378* (2013.01); *A61F 2002/30428* (2013.01); *A61F 2002/30538* (2013.01); *A61F 2002/30566* (2013.01); *A61F 2002/30617* (2013.01); *A61F 2002/30843* (2013.01); *A61F 2002/4629* (2013.01)

(58) Field of Classification Search
CPC .................. A61F 2/4465; A61F 2/4611; A61F 2002/4475; A61F 2002/2835; A61F 2002/30378; A61F 2002/30428; A61F 2002/30538; A61F 2002/30566; A61F 2002/30617; A61F 2002/30843; A61F 2002/3093; A61F 2002/4629
USPC ...................... 623/17.11–17.16; 606/99, 279
See application file for complete search history.

(56) References Cited

U.S. PATENT DOCUMENTS

| | | | | |
|---|---|---|---|---|
| 8,998,924 B2* | 4/2015 | Simpson | ............... | A61F 2/4611 606/105 |
| 9,220,542 B2* | 12/2015 | Kerboul | ............... | A61F 2/4611 |
| 9,795,494 B2* | 10/2017 | Flickinger | ............. | A61F 2/4611 |
| 2003/0028249 A1* | 2/2003 | Baccelli | ............... | A61F 2/4455 623/17.11 |

(Continued)

*Primary Examiner* — Jessica Weiss
(74) *Attorney, Agent, or Firm* — Brainspark Associates, LLC

(57) ABSTRACT

An intervertebral implant may include a superior exterior surface, an inferior exterior surface, a first exterior lateral surface, and a second exterior lateral surface. The first and second exterior lateral surfaces may be substantially transverse to the superior and inferior exterior surfaces. The implant may further include a first curved end wall at a first longitudinal extremity of the body. The first curved end wall may include a bore configured to receive a first shaft of a tool. Additionally, the implant may include a second curved end wall at a second longitudinal extremity of the body and an elongated slot extending from a portion of the first curved end wall to a portion of the first exterior lateral surface.

14 Claims, 12 Drawing Sheets

(56) References Cited

U.S. PATENT DOCUMENTS

| | | | |
|---|---|---|---|
| 2005/0203538 A1* | 9/2005 | Lo | A61F 2/30771 |
| | | | 606/99 |
| 2006/0229627 A1* | 10/2006 | Hunt | A61B 17/1659 |
| | | | 606/86 R |
| 2006/0235426 A1* | 10/2006 | Lim | A61F 2/4465 |
| | | | 606/99 |
| 2007/0093850 A1* | 4/2007 | Harris | A61F 2/4611 |
| | | | 606/99 |
| 2008/0027544 A1* | 1/2008 | Melkent | A61F 2/442 |
| | | | 623/17.11 |
| 2008/0077241 A1* | 3/2008 | Nguyen | A61B 17/1659 |
| | | | 623/17.11 |
| 2008/0091211 A1* | 4/2008 | Gately | A61B 17/1671 |
| | | | 606/99 |
| 2009/0222092 A1* | 9/2009 | Davis | A61F 2/4455 |
| | | | 623/17.11 |
| 2010/0256760 A1* | 10/2010 | Hansell | A61F 2/4465 |
| | | | 623/17.11 |
| 2013/0103102 A1* | 4/2013 | Taylor | A61F 2/4465 |
| | | | 606/86 A |
| 2014/0156008 A1* | 6/2014 | Flickinger | A61F 2/4611 |
| | | | 623/17.16 |
| 2014/0172103 A1* | 6/2014 | O'Neil | A61F 2/447 |
| | | | 623/17.16 |
| 2017/0056194 A1* | 3/2017 | Biedermann | A61F 2/442 |

* cited by examiner

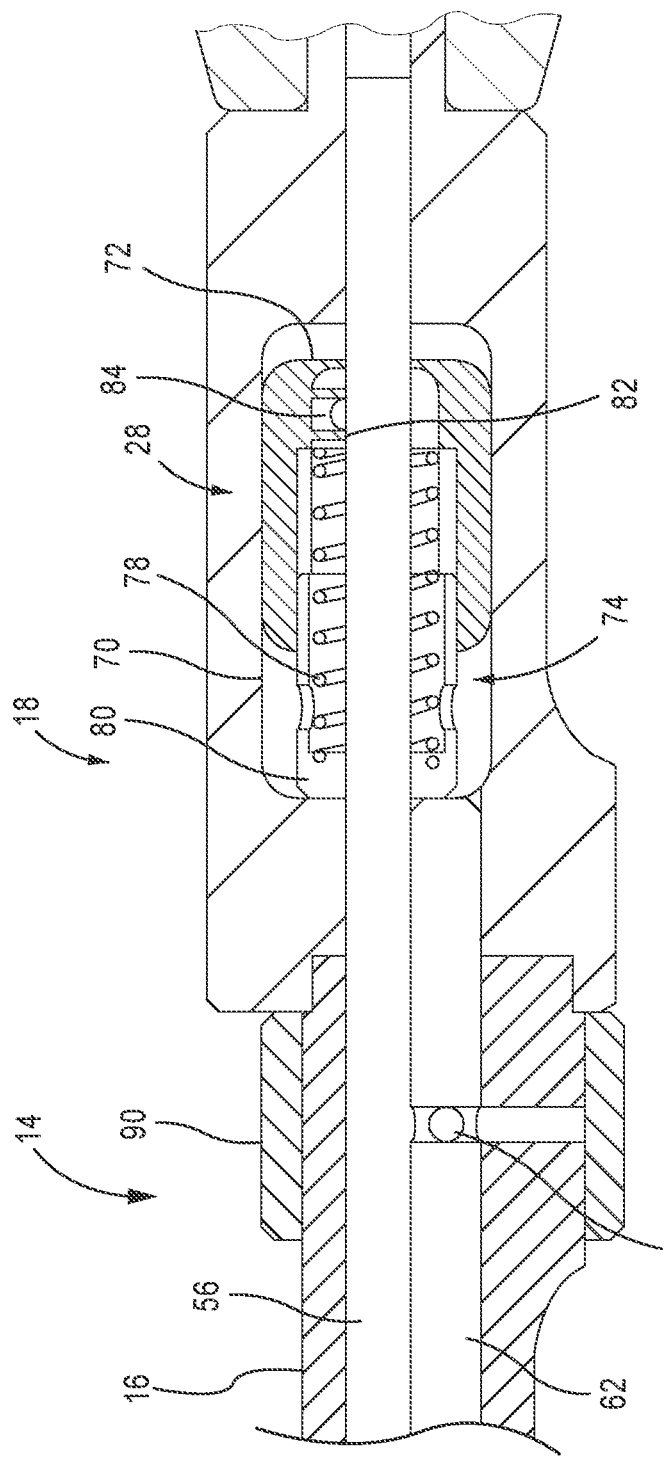

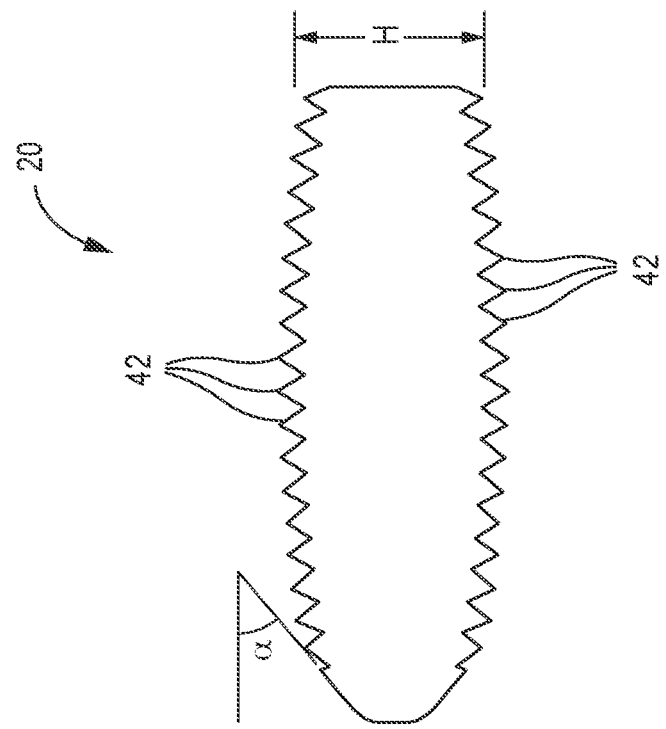
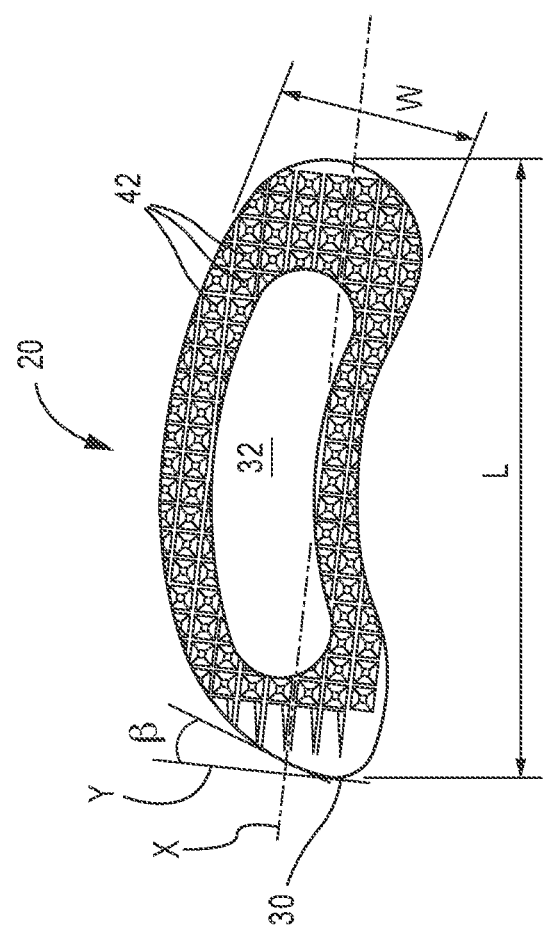
Fig. 9
Fig. 8

ARTICULATING INTERVERTEBRAL DEVICES, RELATED TOOLS, SYSTEMS, AND METHODS

TECHNICAL FIELD

Various aspects of the present disclosure relate generally to intervertebral implants and related systems and methods. More specifically, the present disclosure relates to articulating intervertebral devices, tools, systems, and methods for deployment within a body of a patient.

BACKGROUND

A patient's spinal column includes twenty-six bones called vertebrae which protect the spinal cord. While the shape and/or size of each vertebra varies depending on the placement, loading, posture, and/or pathology within the spinal column, each vertebra is composed of cancellous bone, which is a spongy type of osseous tissue. The cancellous bone of each vertebra is then covered by a thin coating of cortical bone, which is a hard and dense type of osseous tissue. An intervertebral disc is positioned between each pair of adjacent vertebrae in the spinal column. Each disc forms a fibrocartilaginous joint between adjacent vertebrae so as to allow movement of the vertebrae. Beyond enabling relative motion between adjacent vertebrae, each disc acts as a shock absorber for the spinal column.

Each disc comprises a fibrous exterior surrounding an inner gel-like center, which together cooperate to distribute pressure evenly across each disc, which prevents the development of stress concentrations that might otherwise damage and/or impair the vertebrae of the spinal column. However, the discs may be subject to various injuries and/or disorders which may interfere with the disc's ability to adequately distribute pressure and protect the vertebrae. For example, disc herniation, degeneration, and infection may result in insufficient disc thickness and/or support to absorb and/or distribute forces imparted to the spinal column. Disc degeneration, for example, may result when the inner gel-like center begins to dehydrate, which may result in a degenerated disc having decreased thickness. This decreased thickness may limit the ability of the degenerated disc to absorb shock which, if left untreated, may result in pain and/or vertebral injury.

While pain medication, physical therapy, and other non-operative conditions may alleviate some symptoms, such interventions may not be sufficient for every patient. Accordingly, various procedures have been developed to surgically improve patient quality of life via abatement of pain and/or discomfort. One particularly advantageous procedure includes transforaminal lumbar interbody fusion (TLIF). TLIF may be performed via a minimally invasive technique, thus reducing trauma to the spinal column, and decreasing patient recovery times.

During TLIF, a medical professional may make a small (e.g., between about 1 inch and about 6 inches) incision along a patient's back. Next, one or more portions of the vertebral bone (such as, e.g., a facet joint of adjacent vertebral bodies) may be removed so as to access a disc between adjacent vertebrae. A medical professional then may partially remove the damaged and/or degenerated disc, leaving at least a portion of the disc intact to facilitate guiding an interbody device into the disc space. If necessary, bone graft (including, but not limited to, morselized bone) also may be placed within the disc space to promote fusion. Commonly, a medical professional may enlarge the disc space between adjacent vertebrae via a distraction process. Following removal of a portion of the disc and/or distraction of the disc space, an interbody device (e.g., implant) is positioned in the disc space between adjacent vertebrae. The interbody device may relieve pressure from pinched nerves and provide additional therapeutic effects. In some instances, a medical professional also may implant one or more bone screws and/or rods to provide additional support to the spinal column. Additionally, morselized bone may be placed along the sides of the spinal column to promote fusion.

When a TLIF procedure is performed according to a minimally invasive technique, however, direct vision of the disc space is not available. In addition, it may be difficult to visualize an interbody device during implantation. Accordingly, proper placement of an interbody device along the spinal column may be a difficult and tedious task, often requiring extensive skill and experience. Additionally, it is often the case that the available space (e.g., distance) between two adjacent vertebrae intended to receive an interbody device is smaller than the height of the interbody device chosen for insertion. In such cases, a medical professional may need to distract the disc space to prepare for insertion of the interbody device. Distraction, however, is often done with various tools and implements (e.g., rods, screws, etc.) which may interfere, impede, and/or block an interbody device's insertion and/or entrance into the disc space. Accordingly, it may be difficult to guide the interbody device into position between adjacent vertebrae that have been distracted by conventional methods. If distraction is not performed, however, it may be challenging to insert the interbody device so as to create sufficient space between (e.g., distract) adjacent vertebrae itself, while maintaining control. Further, during insertion of the interbody device, the interbody device may impact remaining portions of the disc and/or bone graft which may interfere with the proper placement of the interbody device.

Thus, there remains a need for improved interbody devices, associated systems, tools, and insertion methods.

SUMMARY

Examples of the present disclosure relate to, among other things, intervertebral implants. Each of the embodiments disclosed herein may include one or more of the features described in connection with any of the other disclosed embodiments.

In one example, an intervertebral implant may include a superior exterior surface, an inferior exterior surface, a first exterior lateral surface, and a second exterior lateral surface. The first and second exterior lateral surfaces may be substantially transverse to the superior and inferior exterior surfaces. The implant may further include a first curved end wall at a first longitudinal extremity of the body. The first curved end wall may include a bore configured to receive a first shaft of a tool. Additionally, the implant may include a second curved end wall at a second longitudinal extremity of the body and an elongated slot extending from a portion of the first curved end wall to a portion of the first exterior lateral surface.

Additionally or alternatively, examples of the implant may include one or more of the following features: the first exterior lateral surface may include at least a central portion having a concavity; the second exterior lateral surface may include at least a central portion having a convexity; the elongated slot may include a T-shaped cross-sectional configuration such that an anterior-posterior dimension of the elongated slot is greater than an anterior-posterior dimension of an opening of the elongated slot; the body may further include a through hole in one or both of the first and second exterior lateral surfaces; the second curved wall may include a leading edge angled relative to a longitudinal axis of the body; each of the superior exterior surface and the inferior exterior surface may include a portion angled relative to the longitudinal axis of the body; the bore may be internally threaded; one or more protrusions may extend from one or both of the superior exterior surface and the inferior exterior surface; the body may include a central through opening; and the elongated slot may be configured to receive and retain a second shaft of the tool.

In another example, a system for performing interbody fusion may include an intervertebral implant. The implant may have a body including a superior exterior surface, an inferior exterior surface, a first exterior lateral surface, and a second exterior lateral surface. The first and second exterior lateral surfaces may be substantially transverse to the superior and inferior exterior surfaces. The body may further include a first curved end wall at a first longitudinal extremity of the body. The first curved end wall may include a bore. Further, the body may include a second curved end wall at a second longitudinal extremity of the body. Additionally, the body may include an articulation groove which may extend from a portion of the first curved end wall to a portion of the first exterior lateral surface. The system may further include a locking shaft which may be configured for selective coupling and uncoupling from the bore. Further, the system may include a shaft which may be configured for selective insertion and retraction from the articulation groove.

Additionally or alternatively, examples of the system may include one or more of the following features: the bore may be internally threaded; a distal end of the locking shaft may be externally threaded; the shaft may include a distal end having an enlarged extension; the shaft may be rotatable between a first configuration and a second configuration, wherein in the first configuration the extension may be oriented such that the extension is configured for insertion within the articulation groove, and wherein, in the second configuration, the extension may be oriented such that the extension is retained within the articulation groove; and the extension may be configured to move within the articulation groove.

In another example, a method for delivering an interbody device may include inserting a body into a prepared disc space between adjacent vertebrae of a patient. The body may include a superior exterior surface, an inferior exterior surface, a first exterior lateral surface, and a second exterior lateral surface. The first exterior lateral surface and the second exterior lateral surface may be substantially transverse to the superior and inferior exterior surfaces. The body may further include a first curved end wall at a first longitudinal extremity of the body and a second curved end wall at a second longitudinal extremity of the body. The first curved end wall may include a bore. Further, an articulation groove may extend from a portion of the first curved end wall to a portion of the first exterior lateral surface. The method may further include uncoupling a locking shaft from the bore and moving a shaft along the articulation groove so as to articulate the body relative to the shaft.

Additionally or alternatively, examples of the method may include one or more of the following features: rotating the shaft relative to the body and removing the articulation shaft from the articulation groove of the body; uncoupling the locking shaft from the bore may include rotating the locking shaft; the bore and locking shaft may be configured to be threadably coupled; and the shaft may include a distal end having an enlarged extension, wherein the shaft may be rotatable between a first configuration and a second configuration, wherein, in the first configuration the extension may be oriented such that the extension is configured for insertion within the articulation groove, and wherein, in the second configuration, the extension may be oriented such that the extension is retained within the articulation groove.

It may be understood that both the foregoing general description and the following detailed description are exemplary and explanatory only and are not restrictive of the disclosure, as claimed.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary arrangements of the present disclosure and together with the description, serve to explain the principles of the disclosure.

FIG. 6A illustrates a cross-sectional view of an exemplary lock actuator and shaft release of the exemplary delivery tool of FIG. 1;

FIG. 8 is a top-view of an additional exemplary interbody device;

FIG. 9 is a side-view of the exemplary interbody device of FIG. 8;

DETAILED DESCRIPTION

Reference now will be made in detail to examples of the present disclosure and illustrated in the accompanying drawings. Wherever possible, the same reference numbers will be used throughout the drawings to refer to the same or like parts.

The terms "proximal" and "distal" are used herein to refer to the relative positions of the components of an exemplary interbody device. When used herein, "proximal" refers to a position relatively closer to the exterior of the body or closer to a medical professional using the interbody device or insertion device. In contrast, "distal" refers to a position relatively further away from the medical professional using the interbody device or insertion device, or closer to the interior of the body. With specific reference to the interbody device(s) disclosed herein, the terms "proximal" and "distal" are used to describe relative portions of an interbody device when coupled to the delivery tool described below.

Figure 1:
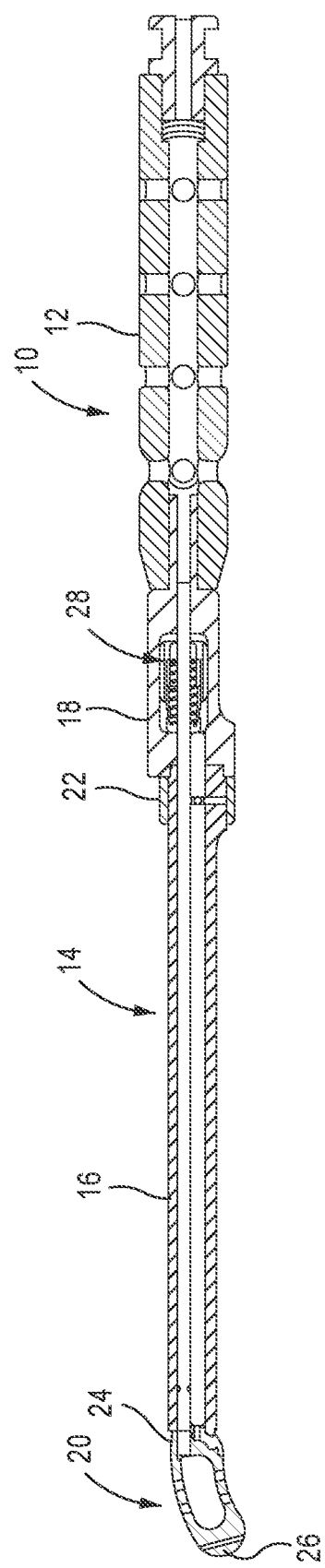
FIG. 1 illustrates an exemplary interbody device coupled to an exemplary delivery tool.

With reference now to FIG. 1, an exemplary delivery tool 10 is selectively coupled to an exemplary interbody device 20. As shown, delivery tool 10 may include a handle 12 coupled to and extending proximally of a shaft 14. An outer surface of handle 12 may be roughened, textured, notched, slotted, etched, sand-blasted, coated or otherwise modified to provide a better gripping surface. Shaft 14 may include a distal portion 16 configured for insertion into a patient's spinal column, as will be described in further detail below. A proximal portion 18 of shaft 14 may house, enclose, or otherwise support a lock actuator 28 and a shaft release 22, as will be described in further detail below.

Interbody device 20 may be comprised of any one or more of metal, metal alloys, plastics, ceramics, and elastomers capable of supporting one or more vertebrae of a patient's spinal column. In some embodiments, interbody device 20 may be made of a composite material embedded with radiopaque components to provide interbody device 20 with radiopacity when visualized with x-ray or fluoroscopic imaging techniques.

Figure 2B:
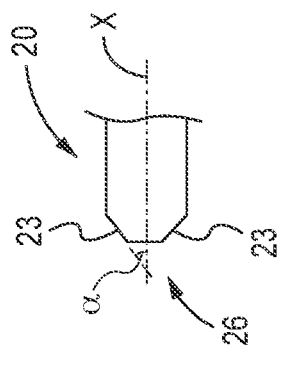
FIGS. 2A-2C illustrate various views of the exemplary interbody device of FIG. 1.
Figure 2C:
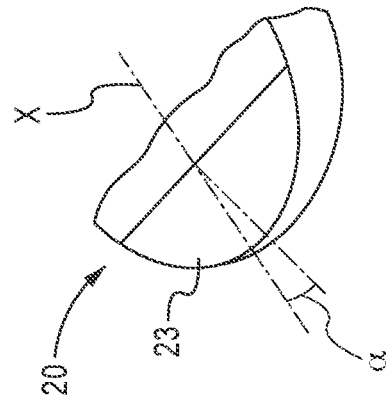
Figure 2A:
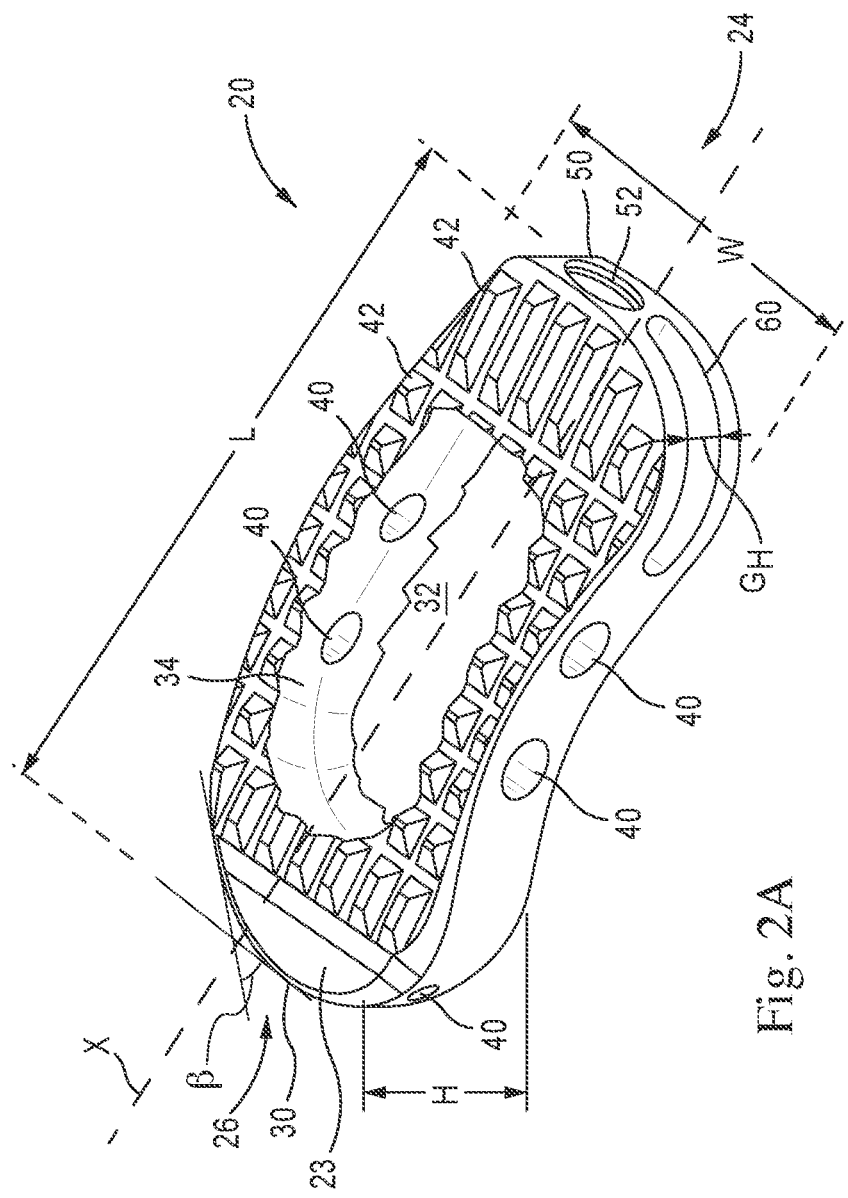

Turning to FIGS. 2A-2C, interbody device 20 may be appropriately sized for a particular patient's needs and/or to achieve a desired therapeutic effect. For example, in some arrangements, interbody device 20 may have a width W between about 8 mm and about 15 mm. Further, interbody device 20 may have a length L between about 25 mm and about 40 mm. Moreover, a height H of interbody device 20 may be between about 5 mm and about 25 mm. Additionally, interbody device 20 may have an angle of lordosis between about 0° and about 15°. That is, the superior exterior and inferior exterior surfaces of interbody device 20 may be sloped or angled towards one another between the first and second exterior lateral surfaces. As used herein, the terms "about," "substantially," and "approximately," may indicate a range of values within +/−20% of a stated value.

As shown in FIG. 2A, interbody device 20 may include a superior exterior surface and an inferior exterior surface. Additionally, interbody device 20 may include first and second exterior lateral surfaces along the length of interbody device 20. As shown, one of the first and second exterior lateral surfaces may define a concavity while the other may define a convexity. Alternatively, in some arrangements, one of the first and second exterior lateral surfaces may define a convexity, while the other of the first and second exterior lateral surfaces may define a substantially flat planar surface, or a plurality of substantially flat planar surfaces. As shown, each of the first and second exterior lateral surfaces may extend in a substantially transverse direction relative to the superior and inferior exterior surfaces of interbody device 20. Interbody device 20 may also include a proximal end 24 configured to be selectively coupled and uncoupled from delivery tool 10, as will be described in further detail below. Proximal end 24 may include a curved wall along a first longitudinal extremity of interbody device 20. Further, a distal end 26 of interbody device 20 may include a curved wall at a second longitudinal extremity of interbody device 20 and may include a tapered leading edge 30. For example, each of the superior and inferior exterior surfaces adjacent leading edge 30 may be tapered at an angle α (FIG. 2B) relative to a longitudinal axis X of interbody device 20 so as to define sloped superior and/or inferior surfaces 23 (FIGS. 2B and 2C), which enable smooth and controlled insertion of interbody device 20, with or without distraction, between adjacent vertebrae. That is, angle α may be selected such that as interbody device 20 is inserted into empty disc space between adjacent vertebrae, sloped superior and/or inferior surfaces 23 may guide interbody device 20 towards a desired position. In some arrangements, as shown in FIG. 2B, angle α may be between about 30° and about 60°. For example, angle α may be about 45°. Additionally, leading edge 30 may be tapered at an angle β relative to an anterior-most surface of interbody device 20. That is, leading edge 30 may be angled relative to an axis Y extending substantially normal to the longitudinal axis X of interbody device 20. Accordingly, during insertion into the empty disc space, leading edge 30 may impact remaining disc material and/or bone graft positioned between the adjacent vertebrae. Upon impaction, further advancement of interbody device 20 by a medical professional may cause interbody device 20 to pivot, rotate, and/or articulate. Accordingly, angle α may be selected so as to control the degree of articulation of interbody device 20 upon impaction. In some arrangements, angles α and/or β may be relatively small thereby enabling smooth distraction of the disc space and controlled insertion of interbody device 20 between adjacent vertebrae so as to avoid potentially damaging kinetic motion during the impaction and/or distraction. Alternatively, angle α and/or β may be relatively large or aggressive thereby enabling insertion of interbody device 20 between adjacent vertebrae without the need to distract the disc space. By way of example only, as shown in FIG. 8, angle β may be relatively larger or aggressive in comparison the arrangement depicted in FIG. 2A.

Figure 10:
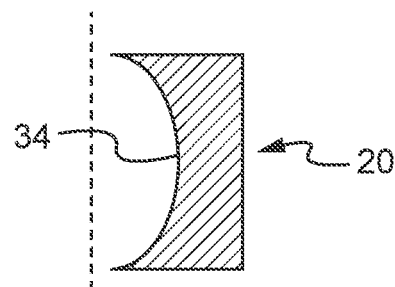
FIGS. 10-12 illustrate various cross-sectional arrangements of an inner wall of the exemplary interbody device of FIG. 1.
Figure 11:
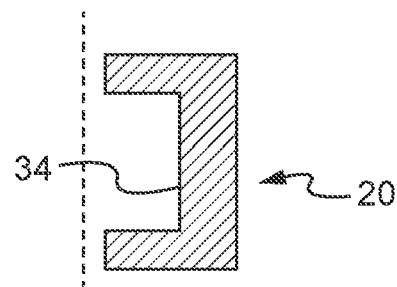
Figure 12:
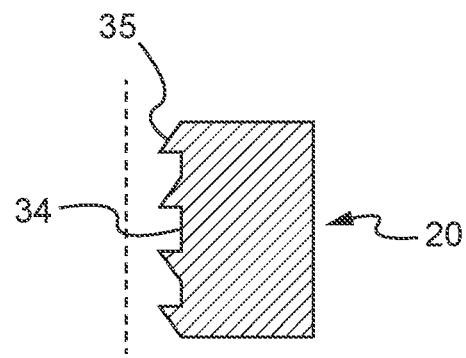

With continuing reference to FIG. 2A, interbody device 20 may define a generally central space 32 or through opening. Space 32 may be configured so as to receive and retain bone graft material (not shown) therein. For example, bone graft material may be packed within space 32 so as to facilitate ossification of bone and subsequent fusion of adjacent vertebrae. In order to ensure bone graft material inserted within space 32 remains therein, interbody device 20 may include one or more retention features. For example, an internal geometry of interbody device 20 may be configured such that bone graft material packed within interbody device 20 may be prevented from dislodging from and/or falling out of space 32. That is, interior surface(s) of interbody device 20 defining space 32 may define one or more non-uniform or uneven surfaces which, upon receipt of bone graft material, may act to hold bone graft material therein. For example, as shown in FIGS. 2A and 10, one or more inner walls 34 of interbody device 20 may be rounded, curved, or otherwise define a wall concavity. Alternatively, as shown in FIG. 11, one or more inner walls 34 of interbody device 20 may form a planar wall recess. Still further, in some examples, as shown in FIG. 12, one or more inner walls 34 of interbody device 20 may include one or more serrations, teeth, or protrusions 35 thereon. In addition, due to the geometric irregularity (e.g., concavity, planar recess, and/or serrations) of walls 34, walls 34 may define a lip extending slightly over space 32 so as to retain bone graft material therein. Accordingly, due to the irregularity of wall(s) 34, and or the other features described herein, bone graft material received within space 32 may be maintained therein during impaction and/or manipulation of interbody device 20.

Interbody device 20 may further include one or more blood flow passageways 40, as shown in FIG. 2A. Passageways 40 may include bores (e.g., through holes, slots, and/or openings) extending through the walls (e.g., one or more of the first and second lateral exterior surfaces) of interbody device 20 and configured to enable circulation (e.g., fluidly communicate) of blood in and through interbody device 20 and/or bone graft material packed within space 32, which may facilitate improved ossification. Additionally, interbody device 20 may include one or more anti-migration features 42 configured to maintain interbody device 20 within a desired position between adjacent vertebrae. The anti-migration features may be disposed on superior and/or inferior surfaces of interbody device 20. Such features 42 may include any one or more of notches, bumps, tangs, grips, and/or protrusions extending from interbody device 20 and configured to increase a coefficient of friction between interbody device 20 and an endplate of an adjacent vertebral body. Features 42 may include any appropriate configuration, such as, for example, triangular, pyramidal, conical, and/or irregular shapes. Further, it is understood that any combination of geometric shapes and/or arrangement of features 42 may be disposed along any surface of interbody device 20. In some embodiments, anti-migration features 42 may define a plurality of tracking grooves disposed on proximal and/or distal portions of interbody device 20. The tracking grooves may be formed by a plurality of spaced apart elongated features 42 defining valleys between adjacent features. The tracking grooves may assist in inhibiting medial or lateral movement of interbody device 20 during implantation or impaction within narrow disc spaces.

Figure 13:
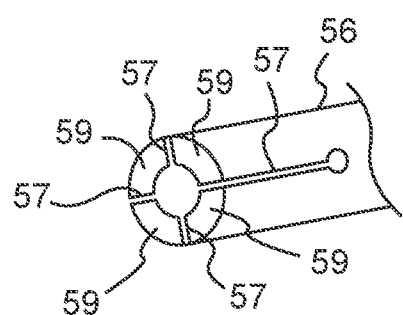
FIGS. 13 and 14 illustrate various views of an alternative coupling arrangement between a shaft and a bore of the exemplary interbody device of FIG. 1.
Figure 14:
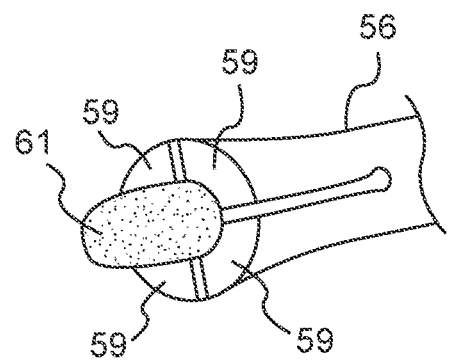

Additionally, interbody device 20 may include a lock bore 50 positioned along a proximal end 24 thereof. Lock bore 50 may be disposed in a first curved end wall (e.g., an exterior side surface) of interbody device 20. Lock bore 50 may be internally (e.g., female) threaded 52 so as to selectively couple and uncouple from an externally (e.g., male) threaded 58 locking shaft 56, as will be described in further detail below. Alternatively, in some arrangements, lock bore 50 can be replaced with an externally (e.g., male) threaded protrusion configured to be received in an internally (e.g., female) threaded opening in a distal end of the locking shaft 56. In an alternative arrangement, as shown in FIGS. 13 and 14, locking shaft 56 may be hollow and radially expandable. That is, as shown, locking shaft 56 may define a plurality of slots, slits, and/or cuts 57 extending along a distal end thereof. Cuts 57 may define a plurality of petals 59 extending circumferentially about locking shaft 56. In use, the medical professional may insert the distal end of locking shaft 56, including petals 59, within lock bore 50. In order to secure locking shaft 56 relative to lock bore 50, a stylet 61, rod, tube, or similar member may be passed through a lumen defined by the hollow locking shaft 56. At least a portion (e.g., tip, head, or distal end) of stylet 61 may have an diameter such that, when positioned within the lumen of locking shaft 56 adjacent petals 59 may be urged radially outwardly. With petals 59 expanded radially outwardly so as to abut internal circumferential surfaces of lock bore 56, locking shaft 56 may be fixed relative to lock bore 50.

Figure 4:
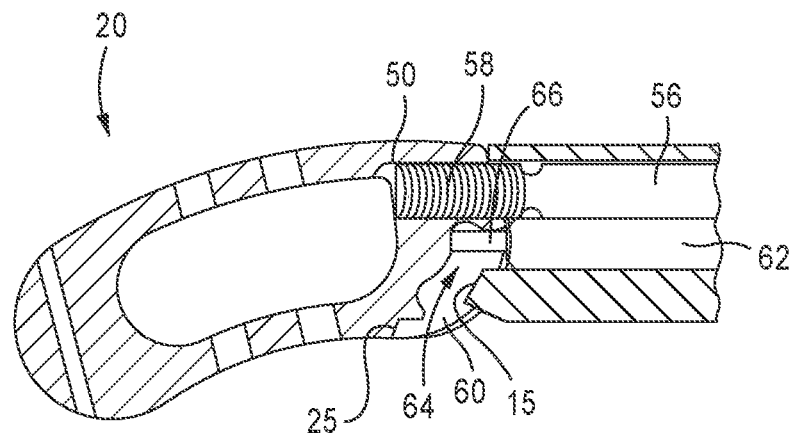
FIG. 4 illustrates a distal end of the exemplary delivery tool of FIG. 1, in a locked configuration, and coupled to the exemplary interbody device of FIG. 2.

Lock bore 50 may extend distally from proximal end 24 towards and into space 32 (FIG. 4). Additionally, interbody device 20 may include an articulation groove 60 extending distally from proximal end 24 and around a side (e.g., an exterior lateral surface) of interbody device 20. Articulation groove 60 also may be disposed in a side surface of interbody device 20. For example, articulation groove 60 may extend from a portion of the first curved wall of proximal end 24 towards and along a lateral exterior surface of interbody device 20. As shown in FIG. 2A, articulation groove 60 may be disposed in the same side surface as lock bore 50 and spaced therefrom. In some arrangements, articulation groove 60 may have a T-shaped cross-section such that an anterior-posterior dimension of the articulation groove 60 is greater than an anterior-posterior dimension of an opening to articulation groove 60. For example, articulation groove 60 may have a depth configured (e.g., sized and/or shaped) so as to receive a distal end 64 of a shaft 62 therein. For example, articulation groove 60 may define an elongate opening having a height $G_H$. Height $G_H$ may be sufficient so as to allow insertion and retraction of distal end 64 of shaft 62 into and/or from articulation groove 60 in a first configuration, while preventing insertion and retraction of distal end 64 of shaft 62 into and/or from articulation groove 60 in a second configuration, as will be described in further detail below. Additionally or alternatively, articulation groove 60 may have any appropriate cross-sectional shape in the anterior-posterior direction so as to selectively retain shaft 62 therein and permit retraction of shaft 62 therefrom. That is, in some arrangements, articulation groove 60 may define a rounded, dove-tailed, or other such key or small opening configured to cooperate with a corresponding geometric feature of shaft 62.

Figure 3:
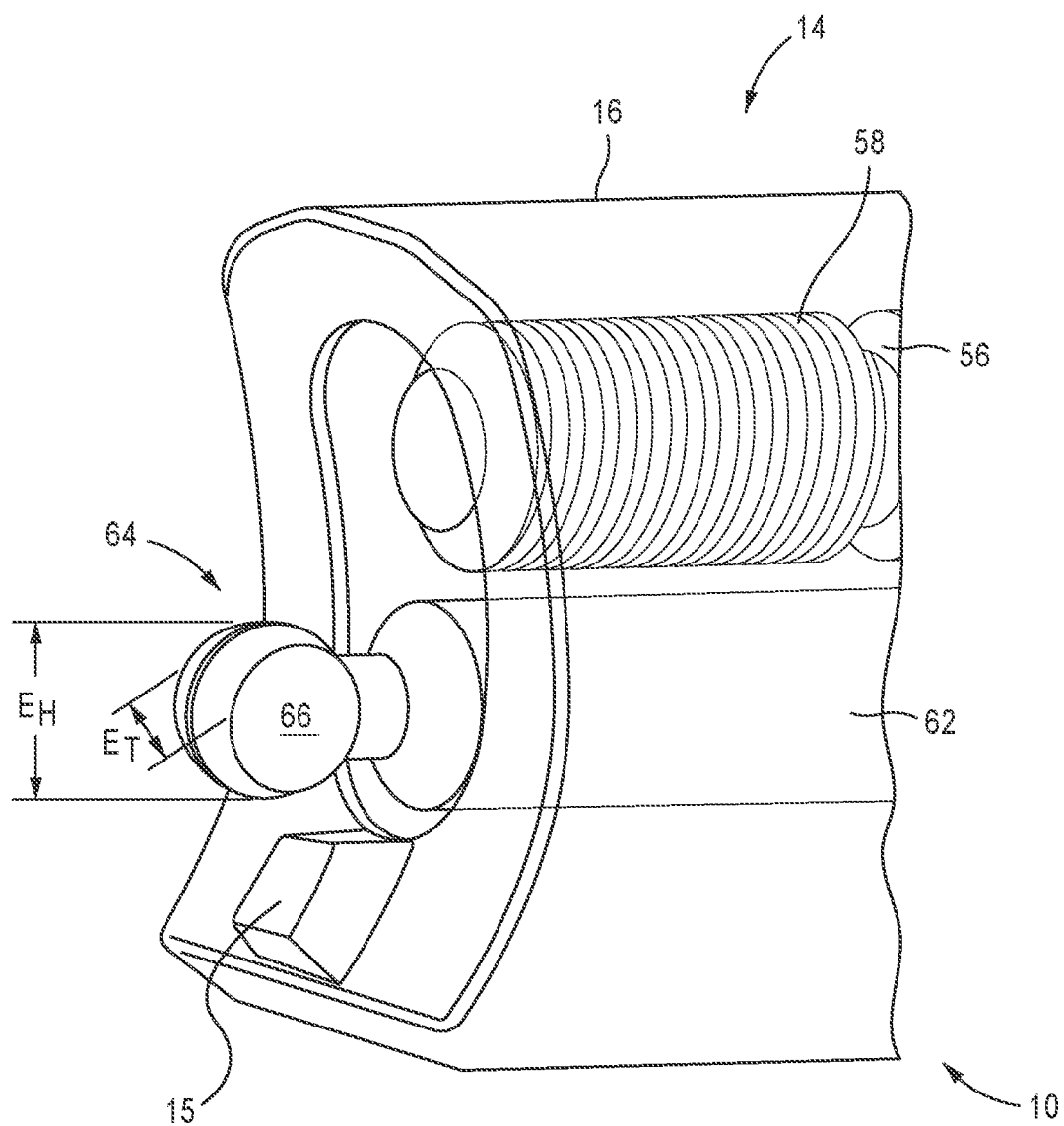
FIG. 3 is a perspective view of a distal end of the exemplary delivery tool of FIG. 1.

For example, FIG. 3 illustrates a perspective view of a distal end of a delivery tool 10 uncoupled from interbody device 20. As shown in FIGS. 1 and 3, externally threaded 58 locking shaft 56 may extend along shaft 14. Locking shaft 56 may be rotatable relative to shaft 14 so as to selectively couple and decouple from interbody device 20. For example, external threading 58 of locking shaft may cooperate, mate, and/or otherwise engage internal threading 52 of lock bore 50. That is, locking shaft 56 may be rotated a first direction so as to selectively couple and/or engage external threading 58 of locking shaft 56 with internal threading 52 of lock bore 50. Additionally, locking shaft 56 may be rotated in a second direction, opposite the first direction, so as to selectively decouple and/or disengage external threading 58 of locking shaft 56 from internal threading 52 of lock bore 50. Locking shaft 56 may be rotated relative to shaft 14 via any appropriate mechanism, as will be described in further detail below. In addition, locking shaft 56 may be selectively extended out of and withdrawn into shaft 14. That is to say, locking shaft 56 may be axially translatable relative to shaft 14. Locking shaft may be rotated and/or axially translated relative to shaft 14 via any appropriate mechanism, as will be described in further detail below.

Further, as shown in FIGS. 1, 3, and 5A-5C, shaft 62 may extend along shaft 14. Shaft 62 may be axially translatable and rotatable relative to shaft 14 so as to selectively couple and decouple from interbody device 20. That is, shaft 62 may be rotated a first direction so as to selectively couple and/or engage distal end 64 of shaft 62 with articulation groove 60. Additionally, shaft 62 may be rotated in a second direction, opposite the first direction, so as to selectively decouple and/or disengage distal end 64 of shaft 62 from within articulation groove 60. For example, distal end 64 of shaft 62 may include a disc, lobe, bulb, wheel, or other such extension 66. Extension 66 may have a thickness $E_T$ and height $E_H$ configured for insertion within articulation groove 60. For example, in a first configuration, extension 66 may be aligned such that the thickness $E_T$ direction of extension 66 extends generally parallel to the groove height $G_H$ direction of articulation groove 60. Thickness $E_T$ of extension 66 may be smaller than groove height $G_H$. Accordingly, in the first configuration (FIG. 5C), extension 66 may be passed into and received within or removed from articulation groove 60 with sufficient clearance. In such a manner, extension 66 may be freely inserted into or removed from articulation groove 60. Once inserted into articulation groove 60, extension 66 may be configured to slidingly move within groove 66 as desired. That is, extension 66 may be appropriately dimensioned so as to move reciprocally, as desired, within articulation groove 60. In a second configuration, shaft 62, and therefore, extension 66, may be rotated approximately 90°. Accordingly, the thickness $E_T$ direction of extension 66 may extend generally perpendicular to the groove height $G_H$ direction of articulation groove 60, while the height $E_H$ direction of extension 66 extends generally parallel to the groove height $G_H$ direction of articulation groove 60. Height $E_H$ of extension 66 may be larger than groove height $G_H$. Accordingly, in the second configuration (FIG. 5B), extension 66 may be prevented from being removed from (e.g., pulled out of) articulation groove 60 via interaction between extension 66 and articulation groove 60. Shaft 62 may be rotated and/or axially translated relative to shaft 14 via any appropriate mechanism, as will be described in further detail below.

In addition, as shown in FIG. 3, a distal surface of shaft 14 may be configured to complement a portion of interbody device 20. For example, the distal surface of shaft 14 may include a curvature that corresponds to the curvature of a proximal end of interbody device 20. Additionally, a distal surface of shaft 14 may include an extension 15 configured to cooperate with a proximal end of interbody device 20 so as to limit articulation and/or rotation of interbody device 20 relative to shaft 14 beyond a desired amount, as will be described in further detail below. Further, as shown in FIG. 3, each of locking shaft 56 and shaft 62 may extend through a common lumen. Accordingly, the lumen of shaft 14 may be elongated and/or ovular so as to accommodate multiple shafts therethrough. However, in some arrangements, shaft 14 may define a plurality of lumens. According, each of locking shaft 56 and shaft 62 may extend through a separate and distinct lumen of shaft 14. Shaft 14 may also include any appropriate visualization, illumination, irrigation, aspiration, and other such lumens configured to deliver one or more tools, fluids, or other materials to a distal end of shaft 14. Still further, in some arrangements, locking shaft 56 may extend through a lumen of a first delivery tool 10, while shaft 62 may extend through a lumen of a second delivery tool 10, different than the first tool.

Figure 5A:
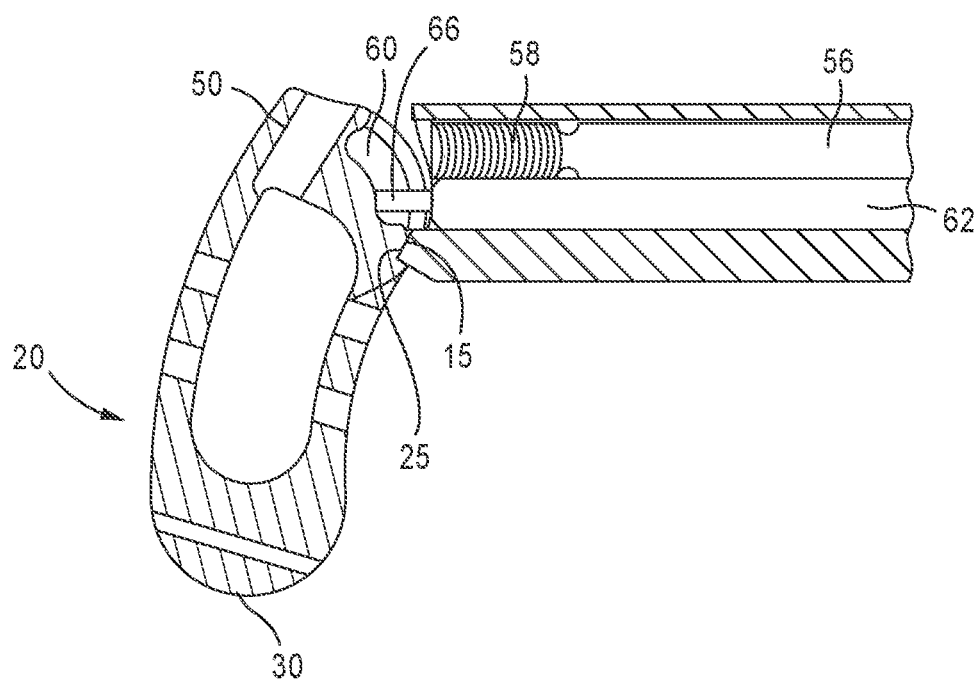
FIG. 5A illustrates a distal end of the exemplary delivery tool of FIG. 1, in an unlocked configuration, and coupled to the exemplary interbody device of FIG. 2 when articulated relative to the delivery tool.
Figure 5B:
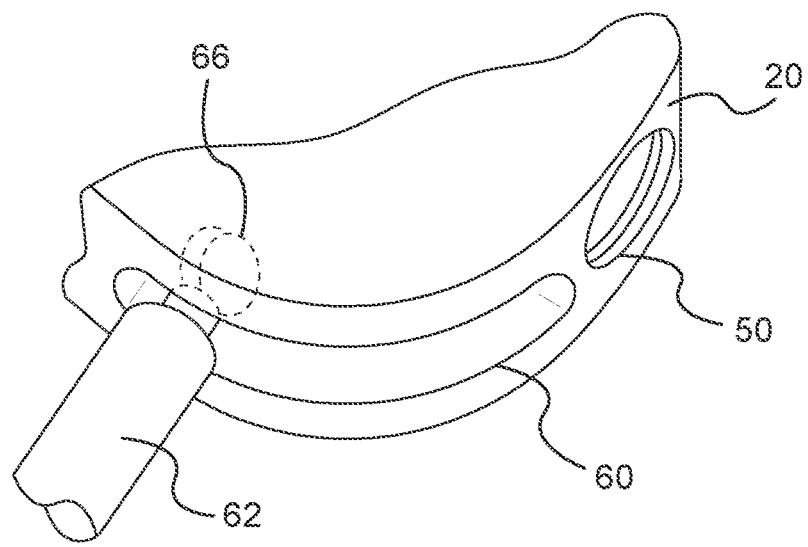
FIGS. 5B and 5C illustrate an exemplary shaft of the delivery tool in a first state within the exemplary interbody device of FIG. 2, and a second state for removal from and insertion into the exemplary interbody device of FIG. 2, respectively.

FIGS. 4 and 5A-5C illustrate the exemplary delivery tool 10 of FIG. 1 coupled to interbody device 20 in a locked and unlocked configuration, respectively. For example, in the locked configuration of locking shaft 56, as shown in FIG. 4, external threading 58 of locking shaft 56 may be engaged with internal threading 52 of lock bore 50 such that interbody device 20 is securely coupled to delivery tool 10. That is, a distal end of locking shaft may be extended out of shaft 14 and threadingly coupled to lock bore 50. Additionally, after insertion of extension 66 into articulation groove 60, shaft 62 may be rotated towards the second configuration such that extension 66 may be prevented from being removed from (e.g., pulled out of) articulation groove 60 via interaction between extension 66 and articulation groove 60, as shown in FIG. 5B (in which locking shaft 56 and shaft 14 have been omitted for clarity). In such a manner, extension 66 of shaft 62 may be retained within articulation slot 60 to enable articulation of interbody device 20 relative to shaft 62 of delivery tool 10 during insertion and/or impaction between adjacent vertebrae.

Figure 5C:
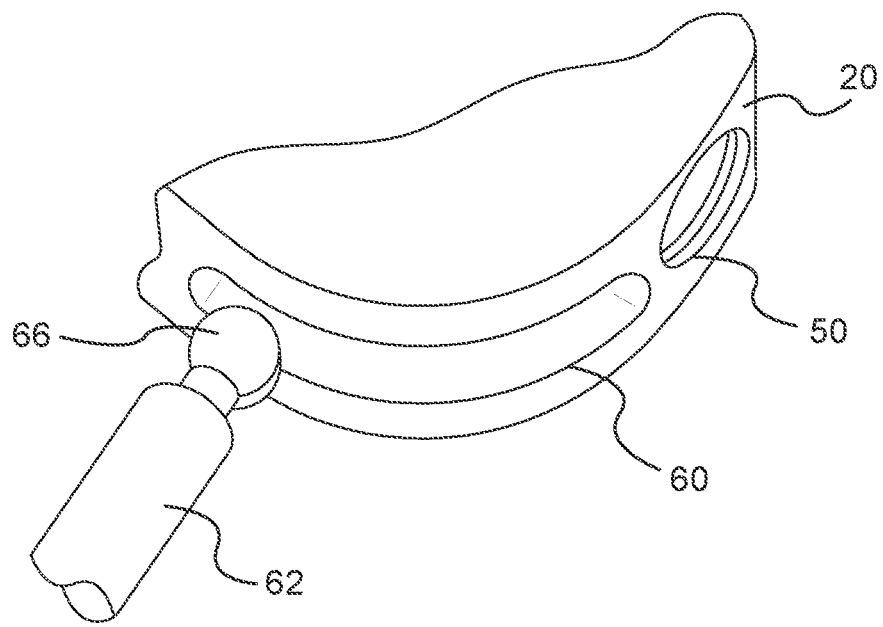

Indeed, during insertion of interbody device 20 between adjacent vertebrae, shaft 56 may be maintained in the locked configuration so as to enable a medical professional increased control and rigidity during delivery. Once interbody device 20 is at least partially inserted between adjacent vertebrae, locking shaft 56 may be rotated so as to decouple and/or disengage external threading 58 of locking shaft 56 from internal threading 52 of lock bore 50. Once disengaged, as shown in FIG. 5A-5C, extension 66 may glide, slide, or otherwise move along articulation groove 60 (FIG. 5B), thereby enabling articulation of interbody device 20 relative to shaft 14 of delivery tool 10. Indeed, upon impaction of leading edge 30 with remaining disc material and/or bone graft positioned between the adjacent vertebrae, interbody device 20 may be naturally urged toward an articulated (e.g., bent) configuration. By virtue of coupling between extension 66 and interbody device 20, articulation of interbody device 20 may occur in a controlled manner. That is, delivery tool 10 enables insertion of, and impaction by, interbody device 20 while maintaining dominance over interbody device 20 along all surgical planes. Once interbody device 20 has been positioned at the appropriate location and/or articulated relative to shaft 62, shaft 62 may be rotated such that extension 66 of shaft 62 may be removed from articulation groove 60 as shown in FIG. 5C (in which locking shaft 56 and shaft 14 have been omitted for clarity). To limit articulation of interbody device 20 relative to shaft 62, interbody device 20 may include a recess 25 configured to receive extension 15 therein. That is, recess 25 may include a shape corresponding (e.g., similar) to the shape of extension 15 such that, when interbody device 20 is articulated relative to shaft 62, extension 15 may be received within recess 25. For example, recess 25 may define a slot, trajectory, or guide to control the degree of articulation of interbody device 20 relative to shaft 62. That is, during articulation, extension 15 may ride along recess 25 to prevent overarticulation. Additionally, as recess 25 and extension 15 are correspondingly shaped, recess 25 may prevent extension 15 from rotating relative thereto. That is, recess 25 may maintain or otherwise keep interbody device 20 within a desired plane during articulation, and inhibit or prevent interbody device 20 from rotating away from such a plane of articulation.

Figure 15:
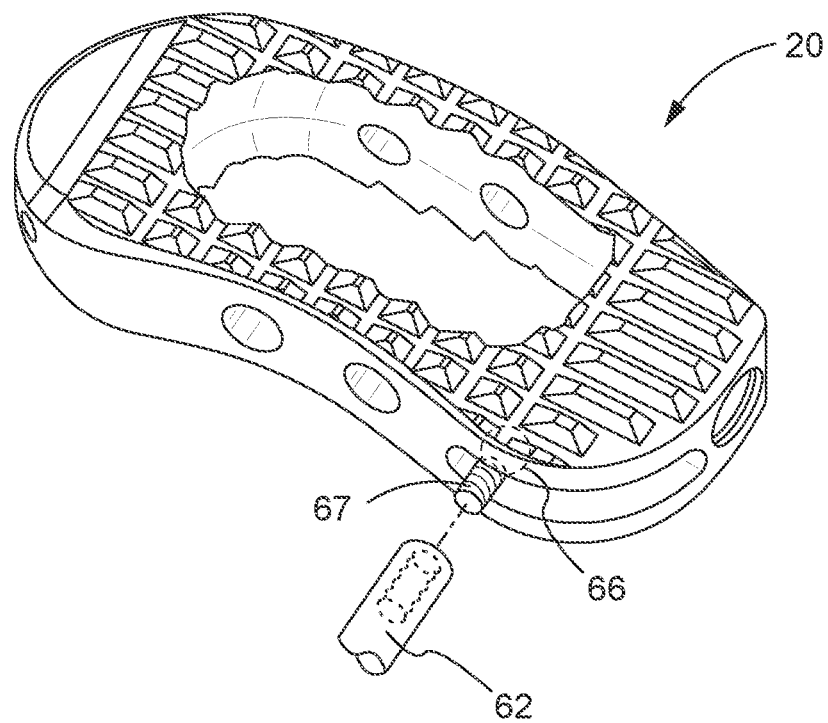
FIGS. 15 and 16 illustrate various views of an alternative coupling arrangement between a shaft and an articulation groove of the exemplary interbody device of FIG. 1.
Figure 16:
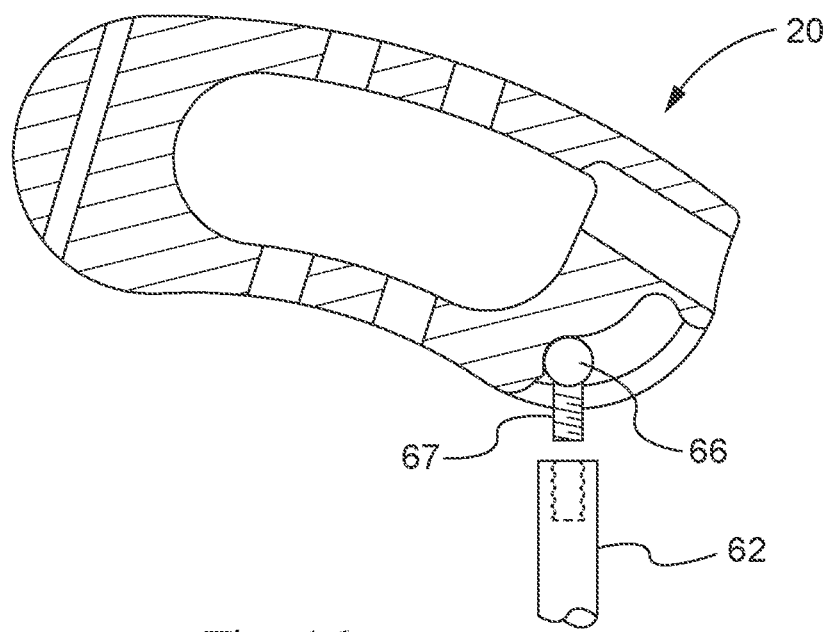

In an alternative arrangement, as shown in FIGS. 15 and 16, shaft 62 may be releasably coupled to extension 66. In such an arrangements, as shown, extension 66 may include an enlarged ball, sphere, bearing, or other such member configured to be non-releasably (e.g., non-removably) received within articulation groove 60. Additionally, extension 66 may include a nipple 67 extending therefrom and configured to cooperate with shaft 62. That is, in some arrangements, nipple 67 may be externally threaded (e.g., male) so as to selectively couple and uncouple from internally threaded (e.g., female) shaft 62. Alternatively, in some arrangements, nipple 67 may be internally threaded (e.g., female) so as to selectively couple and uncouple from an externally threaded (e.g., male) shaft 62. In either arrangement, once interbody device 20 has been positioned at the appropriate location and/or articulated relative to shaft 62, shaft 62 may be rotated so as to be decoupled from nipple 67 as shown in FIGS. 15 and 16.

As noted above, locking shaft 56 may be rotated relative to shaft 14 via any appropriate mechanism. For example, as shown in FIG. 6A, proximal portion 18 of shaft 14 may define an enlarged actuation portion having therein a passageway, aperture, and/or other opening 70 therethrough. The enlarged portion may include any suitable configuration. For example, the enlarged portion may be substantially cylindrical. In other embodiments, the enlarged portion may include a substantially rectangular cross-sectional configuration. As shown, lock actuator 28 may be positioned within opening 70. Lock actuator 28 may include a threaded knob 72 and a continuous push assembly 74, including a spring 78 and a retainer 80. For example, threaded knob 72 may be rotatable about a longitudinal axis of locking shaft 56 against a biasing force of spring 78. Threaded knob 72 may include a substantially cylindrical configuration having an open distal end. The proximal end of threaded knob 72 may be substantially closed with the exception of an opening for locking shaft 56 to pass through. Additionally, threading knob 72 may include an opening 82 in a side wall of threaded knob 72. Opening 82 may be configured to receive, cooperate, and fixedly retain a radially outwardly directed projection 84 or coupling feature extending from locking shaft 56. For example, opening 82 may be configured (e.g., sized and/or shaped) so as to cooperate with (e.g., matingly receive therein) projection 84. As a result of projection 84 being received with opening 82, relative longitudinal motion between locking shaft 56 and threaded knob 72 may be prevented or otherwise limited. In one arrangement, projection 44 may be a semi-hemispherical nub while opening 82 may include a tubular channel. In some embodiments, projection 84 on locking shaft 56 may be replaced with an opening (not shown) for receiving a set screw therein. In such instances, the opening 82 and the opening on locking shaft 56 may be aligned, and a set screw (or other similar fastener) may fixedly couple together threaded knob 72 and locking shaft 56. As a result of the coupling between threaded knob 72 and locking shaft 56 contemplated herein, rotation of threaded knob 72 may be configured to cause likewise rotation of locking shaft 56 due to the interaction between opening 82 and projection 84.

Retainer 80 may include a substantially cylindrical configuration having an open proximal end. A distal end of retainer 80 may be configured to engage (e.g., abut) a distal wall of opening 70. In addition, the distal end of retainer 80 may be substantially closed with the exception of an opening for locking shaft 56 to pass through. Moreover, as shown in FIG. 6A, a distal end of spring 78 (or any other suitable biasing element known in the art) may be received within retainer 80. Similarly, a proximal end of spring 78 may be received within threaded knob 72. As a result of retainer 80 engaging a distal wall of opening 70, spring 78 biases threaded knob 72 (and, consequently, locking shaft 56 as a result of the connection described herein) in the proximal direction.

Rotation and distal urging (e.g., pushing) of threaded knob 72 in a first direction may be configured to move locking shaft 56 against spring 78 and couple and/or engage external threading 58 of locking shaft 56 with internal threading 52 of lock bore 50 of interbody device 20. Additionally, rotation of threading knob 72 in a second direction, opposite the first direction, may be configured to decouple and/or disengage external threading 58 of locking shaft 56 from internal threading 52 of lock bore 50 of interbody 20. Additionally, spring 78 and retainer 80 may be configured to maintain threading knob 72 in position along opening 70. For example, spring 78 may be biased so as to spread apart (e.g., separate) retainer 80 and threading knob 72. In such a manner, interaction between threading knob 72, spring 78 and retainer 80 may maintain threaded knob 72 along a desired position along opening 70.

With continuing reference to FIG. 6A, shaft release 22 may include a knob 90 configured for axial displacement along and rotation about a longitudinal axis of shaft 14. Shaft release 22 may be coupled to shaft 62 via a projection 92. For example, an internal surface of knob 90 may define projection 92 which may in turn, be received and/or mate with a feature (e.g., a hole, opening, or similar irregularity) on shaft 62. Accordingly, rotation and/or axial displacement of knob 90 relative to shaft 14 may cause and/or result in likewise rotation and/or axial displacement of shaft 62. As such, rotation and/or axial displacement of knob 90 in a first direction may be configured so as to selectively couple and/or engage distal end 64 of shaft 62 with articulation groove 60. Additionally, rotation and/or axial displacement of knob 90 in a second direction, opposite the first direction, may be configured so as to decouple and/or disengage distal end 64 of shaft 62 from with articulation groove 60.

Figure 6B:
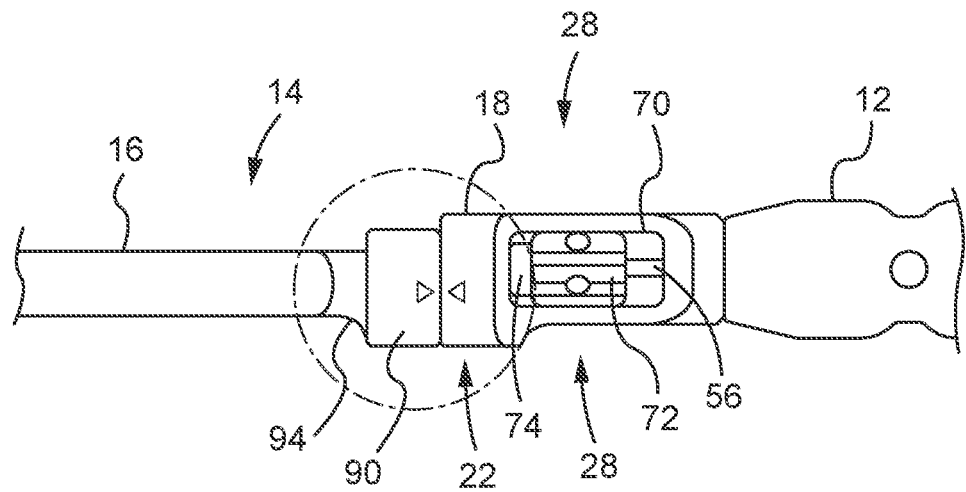
FIG. 6B illustrates a sectional view of the shaft release of FIG. 6A.
Figure 6C:
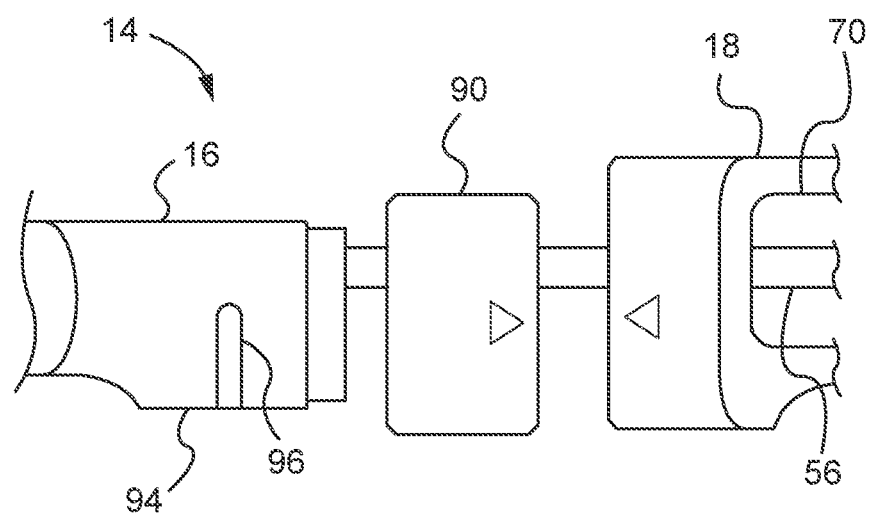
FIG. 6C illustrates an exploded view of the shaft release of FIGS. 6A and 6B.

For example, as shown in FIGS. 6B and 6C, shaft 62 may have a proximal end (not shown) fixedly retained or coupled within a proximal hub 94. Proximal hub 94, may define a passage or slot 96. Slot 96 may extend approximately 90° about a circumferential surface of hub 94. Once assembled, hub 94 may be received within a lumen or other such opening of knob 90 and projection 92 (FIG. 6A) may be received within slot 96 of hub 94. Due to the interaction between projection 92 and slot 96, shaft 62 may be limited to approximately 90° of rotation relative to handle 12 of delivery tool 10. Additionally, as shown, one or more portions, e.g., knob 90 and handle 12, of delivery tool may include indicia 98 or other such markings indicating a position or orientation of shaft 62, and consequently, extension 66. For example, as shown in a first orientation, such indicia 98 may indicate that shaft 62 is in the first configuration (FIG. 5C), in which extension 66 may be passed into and received within or freely removed from articulation groove 60 with sufficient clearance. In a second orientation, such indicia 98 may indicate that shaft 62 is in the second configuration (FIG. 5B), in which extension 66 may be prevented from being removed from (e.g., pulled out of) articulation groove 60 via interaction between extension 66 and articulation groove 60.

Figure 6D:
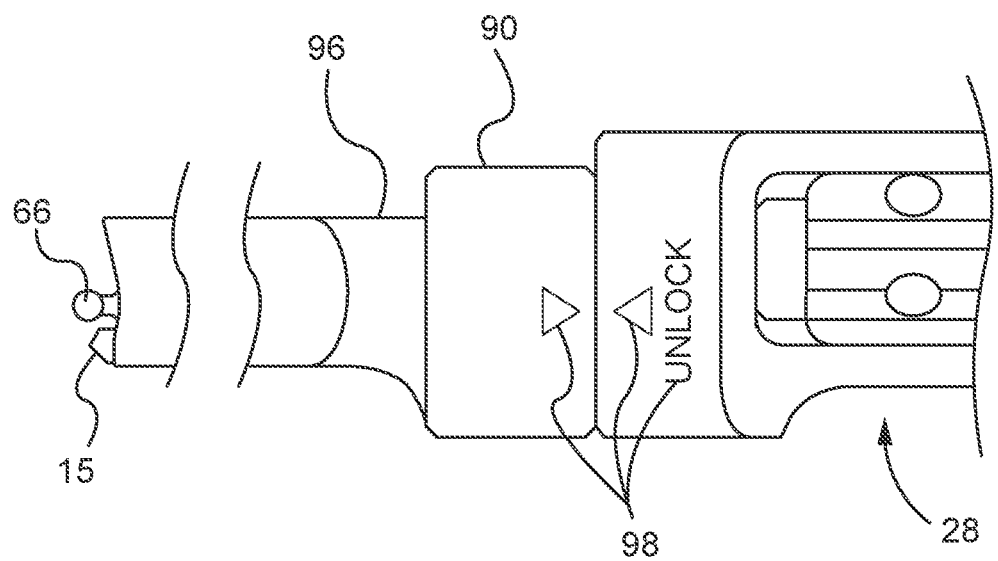
FIGS. 6D and 6E illustrate partial side views of the delivery tool in an unlocked configuration and a locked configuration, respectively.
Figure 6E:
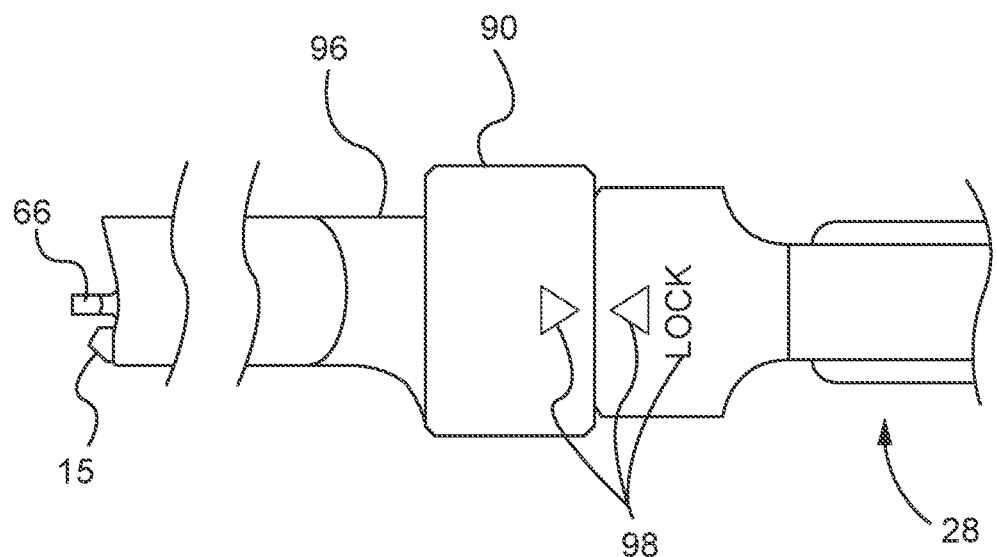

FIGS. 6D and 6E, illustrate partial side views of the delivery tool in an unlocked configuration and a locked configuration, respectively. For example, as shown in FIG. 6D, when indicia 98 are arranged so as to indicate shaft 62 is in the first configuration (e.g., unlocked), extension 66 of shaft 62 may extend from shaft 14 in a first rotational orientation. When, however, knob 90 is rotated such that indicia 98 are arranged to indicate shaft 62 is in the second configuration (e.g., locked), extension 66 of shaft 62 may extend from shaft 14 in a second rotational orientation.

Figure 7A:
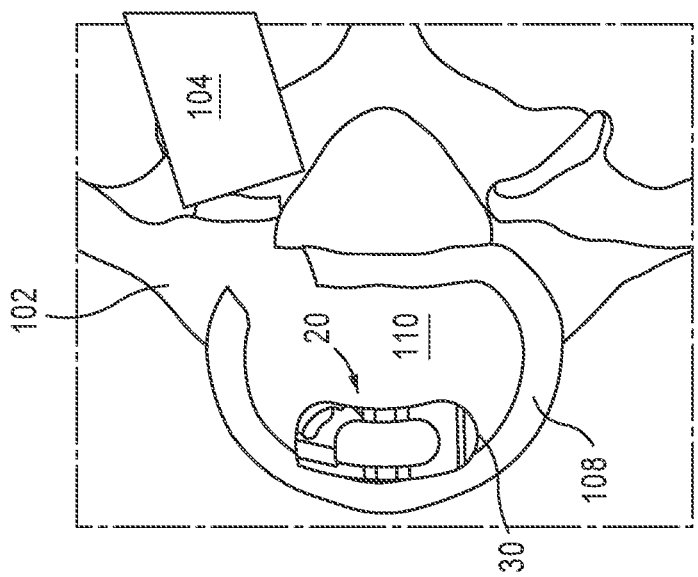
FIGS. 7A-7C illustrate an exemplary method for delivering the exemplary interbody device of FIG. 2.
Figure 7B:
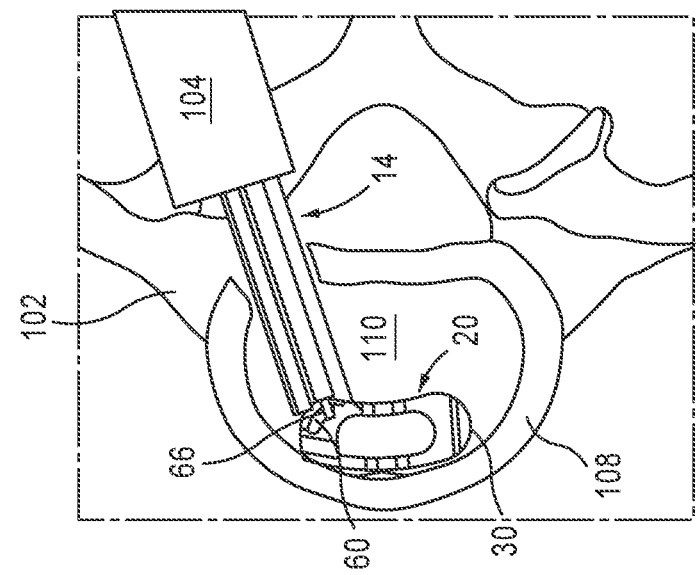
Figure 7C:
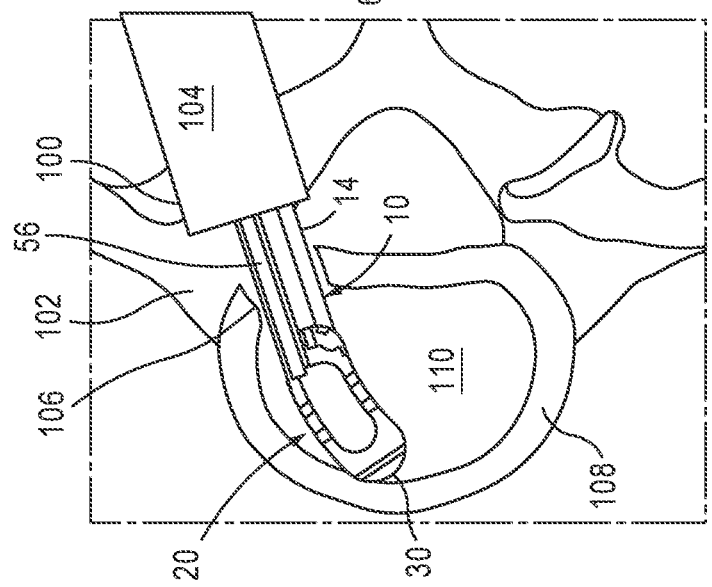

FIGS. 7A-7C illustrate an exemplary method of delivering interbody device 20 between adjacent vertebrae of a patient's spinal column. For example, as discussed above, prior to insertion of interbody device 20, one or more portions of the vertebral bone may be removed so as to access a disc between adjacent vertebrae. That is, a passage 100 extending through one or more vertebrae 102 may be formed, so as to enable insertion of a luminal member 104 therethrough. Luminal member 104 may be any appropriate member configured to introduce delivery tool 10 therethrough. For example, luminal member 104 may include one or more sheaths, tubes, and/or members configured for facilitating low profile delivery of a delivery tool 10. Further, as noted above, a medical professional may then partially remove the damaged and/or degenerated disc, leaving at least a portion of the disc intact to facilitate guiding an interbody device and retaining subsequently implanted bone graft therein. For example, as shown in FIG. 7A, the medical professional may form a passage 106 in a disc 108 so as to provide access to disc space 110 between adjacent vertebrae 102. Thereafter, delivery tool 10 may be extended through passages 100 and 106, distally of luminal member 104, and into disc space 110. During insertion, interbody device 20 may be coupled to shaft 14 of delivery tool 10 in the locked configuration so as to provide the medical professional control over interbody device 20. That is, external threading 58 of locking shaft 56 may be engaged with internal threading 52 of lock bore 50 (FIG. 4) such that interbody device 20 is securely coupled to delivery tool 10. In some embodiments, space 32 of interbody device 120 may be filled with bone graft material prior to insertion of interbody device 120 into disc space 110.

As shown in FIG. 7B, during insertion of interbody device 20 into disc space 110, leading edge 30 may impact remaining disc material and/or bone graft positioned between the adjacent vertebrae 102. Upon impaction, further advancement of interbody device 20 by a medical professional may naturally urge interbody device 20 to pivot, rotate, and/or articulate. Accordingly, locking shaft 56 may be rotated so as to decouple and/or disengage external threading 58 of locking shaft 56 from internal threading 52 of lock bore 50. Once disengaged, as shown in FIG. 7B, extension 66 may glide, slide, or otherwise move along articulation groove 60, thereby enabling articulation of interbody device 20 along disc 108, relative to shaft 14 of delivery tool 10, while allowing the medical professional to maintain control over interbody device 120. That is, by virtue of coupling between extension 66 and interbody device 20, advancement and/or articulation of interbody device 20 may occur in a controlled manner along all surgical planes. Following proper positioning of interbody device 20 within disc space 110, shaft 62, and therefore, extension 66, may be rotated approximately 90° such that the thickness $E_T$ direction of extension 66 may extend generally parallel to the groove height $G_H$ direction of articulation groove 60. Accordingly, extension 66 may be removed from (e.g., pulled out of) articulation groove 60, thereby decoupling or disengaging interbody device 20 from delivery tool 10, as shown in FIG. 7C. Following implantation, morselized bone (or any other ingrowth promoting material) may be added to remaining disc space 110. In some instances, a medical professional may also place morselized bone along the sides of the spinal column to promote fusion.

As shown in FIGS. 8 and 9, interbody device 20 may include a leading edge 30, as discussed above. Leading edge 30 may be tapered at an angle α so as to enable smooth and controlled insertion of interbody device 20, with or without distraction, between adjacent vertebrae. Additionally, leading edge 30 may be tapered at an angle β relative to an anterior-most surface of interbody device 20. That is, leading edge 30 may be angled relative to an axis Y extending substantially normal to the longitudinal axis X of interbody device 20. As noted above, in the arrangement of FIGS. 8 and 9, angle β may be relatively large or aggressive thereby enabling insertion of interbody device 20 between adjacent vertebrae to enable greater control during insertion. Further, as discussed above, angle α may be relatively large or aggressive thereby enabling insertion of interbody device 20 between adjacent vertebrae without the need to distract the disc space. Additionally, as discussed above, interbody device 20 may define a space 32 configured so as to retain bone graft material (not shown) therein. Interbody device 20 may include one or more anti-migration features 42 configured to maintain interbody device 20 within a desired position within between adjacent vertebrae. Such features 42 may include any one or more of notches, bumps, tangs, grips, and/or protrusions extending from interbody device 20. Features 42 may include any appropriate configuration, such as, for example, triangular, pyramidal, conical, and/or irregular shapes. Further, it is understood that any combination of geometric shapes and/or arrangement of features 42 may be disposed along any surface of interbody device 20. For example, as shown in FIG. 9, features 42 may extend along top and bottom (e.g., vertebrae mating) surfaces of interbody device 20.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description.

We claim:

1. A system for performing interbody fusion, the system comprising:
    an intervertebral implant including a body, the body comprising:
        a superior exterior surface;
        an inferior exterior surface;
        a first exterior lateral surface;
        a second exterior lateral surface, wherein the first exterior lateral surface and the second exterior lateral surface are substantially transverse to the superior and inferior exterior surfaces;
        a first curved end wall at a first longitudinal extremity of the body, the first curved end wall including an internally threaded bore;
        a second curved end wall at a second longitudinal extremity of the body;
        an elongated articulation groove spaced apart from the bore, the elongated articulation groove extending from a portion of the first curved end wall to a portion of the first exterior lateral surface; and
    a delivery tool including a first locking shaft configured for selective coupling and uncoupling from the bore of the intervertebral implant, and a second locking shaft configured for selective coupling and uncoupling from the elongated articulation groove of the intervertebral implant independent of the selective coupling and uncoupling of the first locking shaft from the bore of the intervertebral implant, wherein a distal end of the first locking shaft is externally threaded and a distal end of the second locking shaft comprises an enlarged extension, wherein the first and second locking shafts are not coaxial and are each rotatable relative to the intervertebral implant when the intervertebral implant is engaged to the delivery tool.

2. The system of claim 1, wherein the second locking shaft is rotatable between a first configuration and a second configuration, wherein in the first configuration the extension is oriented such that the extension is configured for coupling within the elongated articulation groove, and wherein, in the second configuration, the extension is oriented such that the extension can be uncoupled from the elongated articulation groove.

3. The system of claim 1, wherein the extension is configured to slide within the elongated articulation groove.

4. A system for performing interbody fusion, the system comprising:
an intervertebral implant including a body, the body comprising:
a superior exterior surface;
an inferior exterior surface;
a first exterior lateral surface;
a second exterior lateral surface, wherein the first exterior lateral surface and the second exterior lateral surface are substantially transverse to the superior and inferior exterior surfaces;
a first curved end wall at a first longitudinal extremity of the body, the first curved end wall including an internally threaded bore
a second curved end wall at a second longitudinal extremity of the body; and
an elongated slot extending from a portion of the first curved end wall to a portion of the first exterior lateral surface, the elongated slot spaced apart from the bore; and
a delivery tool including a first locking mechanism having an externally threaded distal for threadably engaging and disengaging from the bore of the intervertebral implant, a second locking mechanism comprising an enlarged distal extension for selectively engaging and disengaging from the elongated slot of the intervertebral implant, and a third locking mechanism comprising a distal tip for engaging the second exterior lateral surface of the intervertebral implant, the first and second locking mechanisms capable of engaging and disengaging independently from one another when the delivery tool is engaged to the intervertebral implant.

5. The system of claim 4, wherein the first exterior lateral surface includes at least a central portion having a concavity.

6. The system of claim 4, wherein the second exterior lateral surface includes at least a central portion having a convexity.

7. The system of claim 4, wherein the elongated slot includes a T-shaped cross-sectional configuration such that an anterior-posterior dimension of the elongated slot is greater than an anterior-posterior dimension of an opening of the elongated slot.

8. The system of claim 4, wherein the body further includes a through hole in one or both of the first and second exterior lateral surfaces.

9. The system of claim 4, wherein the second curved end wall includes a leading edge angled relative to a longitudinal axis of the body.

10. The system of claim 4, wherein each of the superior exterior surface and the inferior exterior surface include a portion angled relative to the longitudinal axis of the body.

11. The system of claim 4, further comprising one or more protrusions extending from one or both of the superior exterior surface and the inferior exterior surface.

12. The system of claim 4, wherein the body includes a central through opening.

13. A system for performing interbody fusion, the system comprising:
an intervertebral implant including a body, the body comprising:
a superior exterior surface;
an inferior exterior surface;
a first exterior lateral surface;
a second exterior lateral surface, wherein the first and second exterior lateral surfaces are substantially transverse to the superior and inferior exterior surfaces;
a first curved end wall at a first longitudinal extremity of the body, the first curved end wall including an internally threaded retention bore and an elongated slot extending away from the retention bore; and
a delivery tool comprising a first elongated shaft having an externally threaded distal tip which threadably engages with the retention bore of the implant, a second elongated shaft comprising an enlarged distal extension which selectively engages with the elongated slot, and a third elongated shaft comprising a distal tip which selectively engages the first curved end wall, and wherein the distal tip of the first elongated shaft, the distal extension of the second elongated shaft and the distal tip of the third elongated shaft are laterally spaced apart from each other.

14. The system of claim 13, wherein the distal extension of the second elongated shaft is rotatable between a first configuration and a second configuration, wherein, in the first configuration, the distal extension is oriented such that the distal extension slides within the retention bore and wherein, in the second configuration, the distal extension is oriented such that the distal extension is retained within the retention bore.

* * * * *